United States Patent [19]

Müller

[11] Patent Number: 5,796,016
[45] Date of Patent: Aug. 18, 1998

[54] DISSOLUTION TESTER

[75] Inventor: Werner G. Müller, Heusenstamm, Germany

[73] Assignee: ERWEKA Gmbh, Heusenstamm, Germany

[21] Appl. No.: 752,991

[22] Filed: Nov. 21, 1996

[30] Foreign Application Priority Data

Dec. 12, 1995 [DE] Germany ............ 295 19 713 U

[51] Int. Cl.⁶ .................. G01N 33/15; B01F 1/00
[52] U.S. Cl. .................. 73/866; 366/140; 366/142; 366/286
[58] Field of Search .............. 73/866, 61.41, 73/61.43, 53.01, 863.31, 863.32, 863.33; 366/140, 142, 207, 261, 286

[56] References Cited

U.S. PATENT DOCUMENTS

| | | | |
|---|---|---|---|
| 3,802,272 | 4/1974 | Bischoff et al. | 366/142 X |
| 4,108,602 | 8/1978 | Hanson et al. | 73/866 X |
| 4,708,023 | 11/1987 | Schneider et al. | 73/863.31 |
| 4,872,353 | 10/1989 | Orr, Jr. et al. | 366/140 X |
| 4,879,917 | 11/1989 | Eppelmann et al. | 73/866 |
| 4,924,716 | 5/1990 | Schneider | 73/866 |
| 5,639,974 | 6/1997 | Hanson et al. | 73/866 |

*Primary Examiner*—Michael Brock
*Attorney, Agent, or Firm*—Evenson, McKeown, Edwards & Lenahan, PLLC

[57] ABSTRACT

A dissolution tester has a plurality of test vessels for receiving dissolution samples and a plurality of stirring elements for stirring the dissolution samples, the stirring elements being disposed in a vertically adjustable housing. A discharging device is provided having discharging tubes for discharging predetermined volume fractions of the dissolution samples to the test vessels. The discharging tubes are disposed at a predetermined working position in the test vessels in accordance with the filling level of the dissolution sample and the stirring element used. The discharging tubes are disposed on a frame and the frame is disposed on the housing in vertically adjustable manner. A stepping motor moves the frame and thus the discharging tubes to the particular working position in program-controlled fashion in accordance with the input data on the filling level and the stirring element. A computing device stores the measurement data and predetermined parameters.

3 Claims, 4 Drawing Sheets

DISSOLUTION TESTER

FIELD OF THE INVENTION

This invention relates to a dissolution tester for testing the dissolution characteristics of test samples.

BACKGROUND OF THE INVENTION

Up to now volume fractions of dissolution samples have been discharged from and returned to devices for testing the dissolution samples, by an operator. This operator is, for example, responsible for properly positioning the discharging tubes of a discharging device in each test vessel of the dissolution tester, whereby the positioning of the discharging tubes of the discharging device depends on the type of stirring tool and on the liquid level of the dissolution sample. The required working position of the discharging tube is at half the height between the upper edge of the stirring element and the filling level line.

The required working position of the discharging tubes of the discharging device can accordingly only be checked visually by the operator. This visual check is dependent, e.g., on parameters such as the visibility of the test vessel, reflection errors caused by the outer wall of the test vessel, as well as on the operator's physical and mental state.

SUMMARY OF THE INVENTION

The main purpose of the present invention is to provide a dissolution tester which permits a reliable, exact positioning of the discharging tubes of a discharging device, which positioning is reproducible and excludes failure by an operator.

This problem is solved by a dissolution tester having a plurality of test vessels for receiving dissolution samples, a plurality of stirring elements for stirring the dissolution samples, the stirring elements being disposed in a vertically adjustable housing. The discharging device has discharging tubes for discharging predetermined volume fractions of the dissolution samples from the test vessels. The discharging tubes are disposed at a predetermined working position in the test vessels in accordance with the filling level of the dissolution sample and the stirring element used. The discharging tubes are disposed on a frame and the frame is disposed on the housing, the frame being vertically adjustable. A motor moves the frame and thus moves the discharging tubes to the particular working position in program-controlled manner in accordance with input data of the filling level and the stirring element. A computing device stores measurement data and predetermined parameters.

This permits exact positioning of the discharging tubes coordinated with the filling level of the dissolution sample and with the type of stirring element used. In accordance with the selected pharmacopoeia and the stirring tools used, the discharging device can be moved to the sampling positions defined by the pharmacopoeia for sample volumes of 500 ml, 750 ml, 900 ml and 1000 ml used in dissolution tests.

A dissolution tester in which the motor is a stepping motor has the advantage that cooperation of the computing device and the motor is facilitated.

A dissolution tester in which the motor is coupled via a toothed belt with two telescopic columns which carry the frame has the advantage that movement of the columns can be accurately controlled.

BRIEF DESCRIPTION OF THE DRAWINGS

An embodiment of the invention will now be described as an example with reference to the enclosed drawings, in which.

DETAILED DESCRIPTION OF THE PREFERRED EMBODIMENTS

Figure 1:
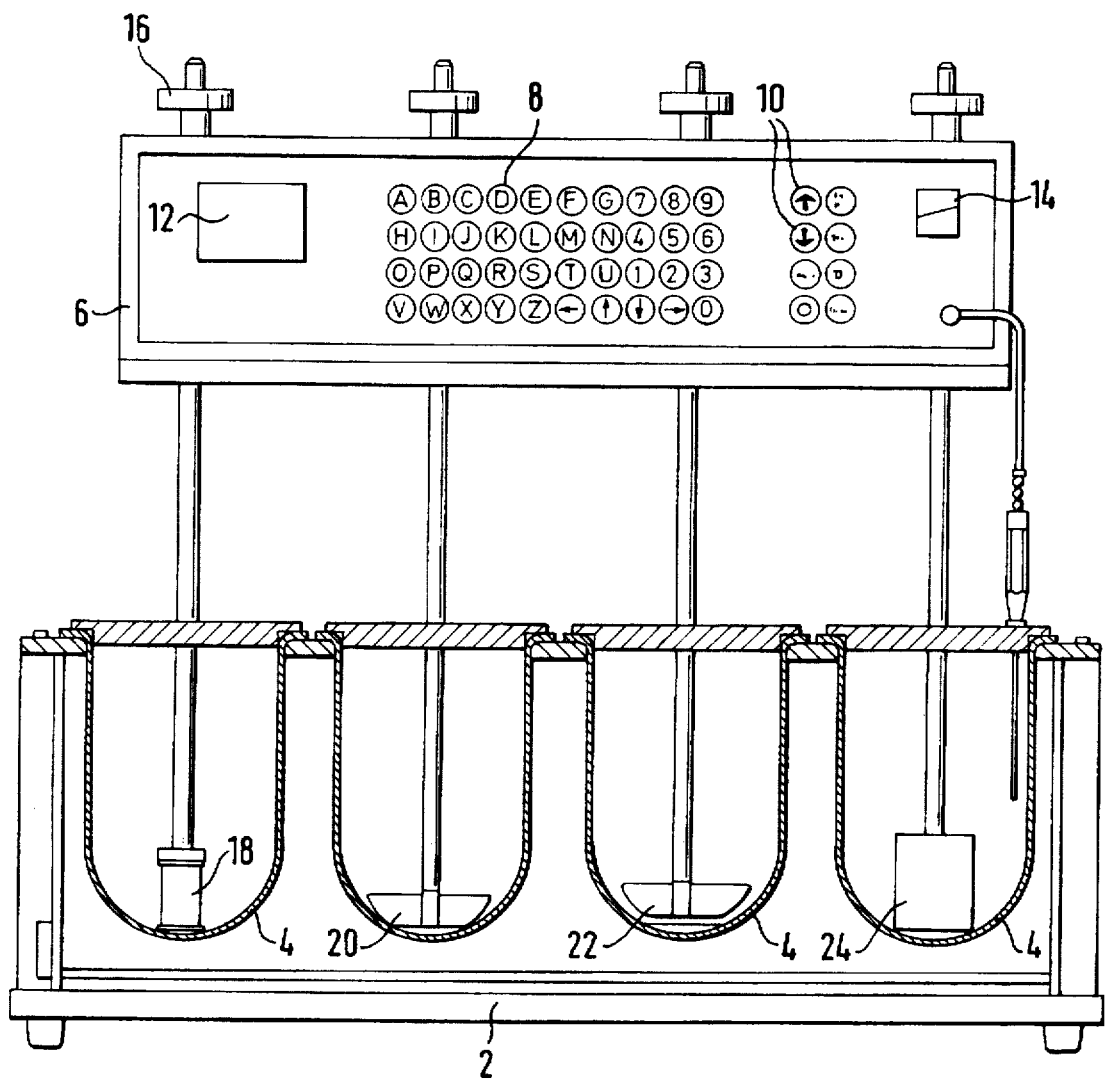
FIG. 1 shows a schematic representation of a dissolution tester during adjustment of the stirring elements.

FIG. 1 shows, schematically, a dissolution tester. The dissolution tester has a rack 2 for test vessels 4 which are disposed in two rows of four vessels each, only the front four test vessels being schematically shown. Disposed above rack 2 is housing 6 adjustable via telescopic columns (not shown) and having a computer control panel 8 for input, control panel 10 for controlling the device, display panel 12, mains plug 14 and clamping devices 16 for mounting stirring tools 18, 20, 22 and 24.

FIG. 1 shows different stirring tools 18 to 24 merely for the sake of illustration; in practice only one type of stirring tool is generally used for a certain test. The different types of stirring tools are associated with different test methods. Tool 18 is a basket stirrer, tool 20 is a paddle stirrer, tool 22 is a paddle stirrer above a disk, and tool 24 is a transthermal cylinder stirrer. When the stirring tools are adjusted they are first moved downward to the position shown in FIG. 1, which is virtually the zero position. After that, the stirring tools are brought a distance of 25±2 mm from the zero position into the working position, as shown in FIG. 2, by moving housing 6.

Figure 3:
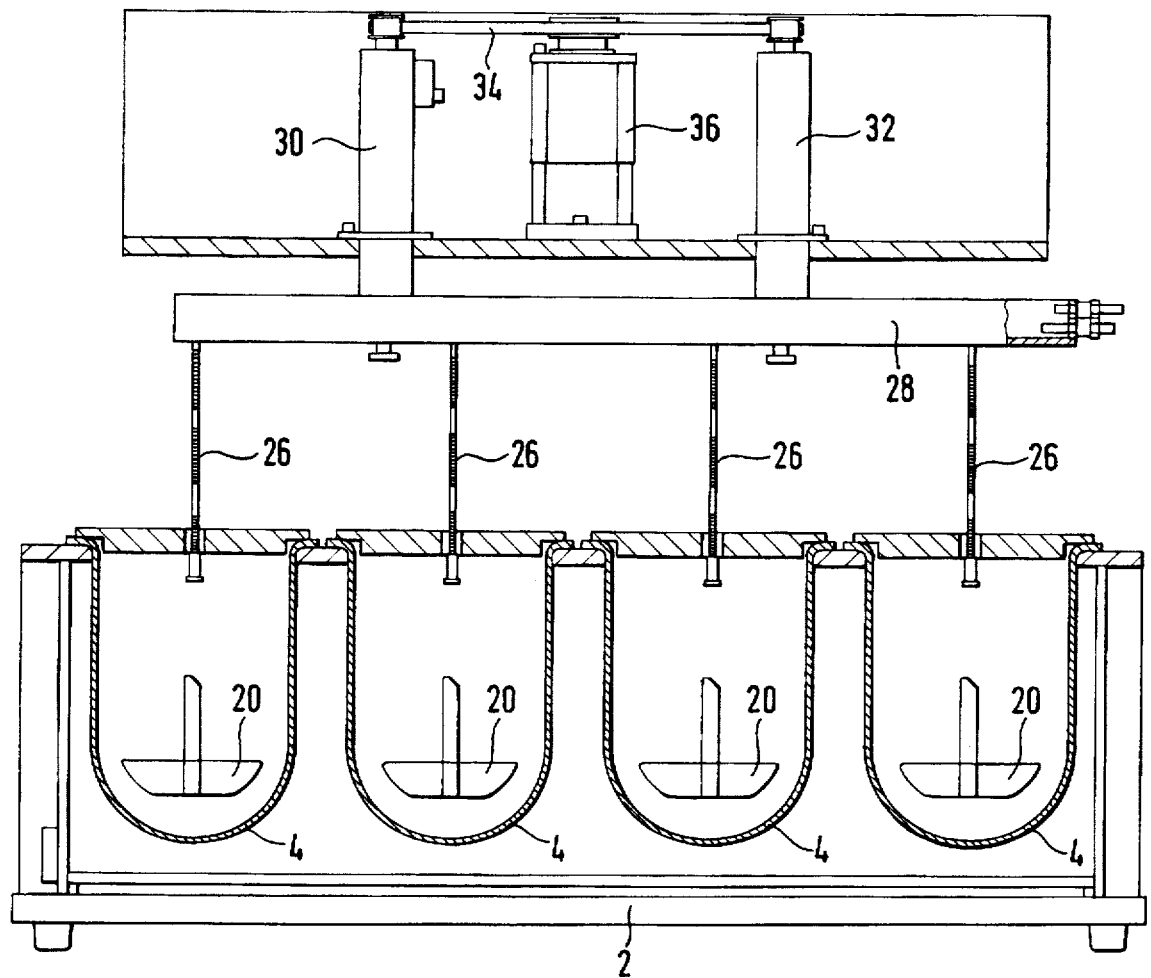
FIG. 3 shows a schematic representation of a device for introducing the discharging tubes into the test vessels, after adjustment of the stirring elements.

The various test specifications require that the discharging tube be brought into position with its discharge opening at half the height between the upper edge of the stirring tool and the test level mark of the sample in the test vessel. FIG. 3 shows stirring tools 20 disposed uniformly in all the test vessels. The stirring tools are in the form of paddles and have been brought into position.

Figure 2:
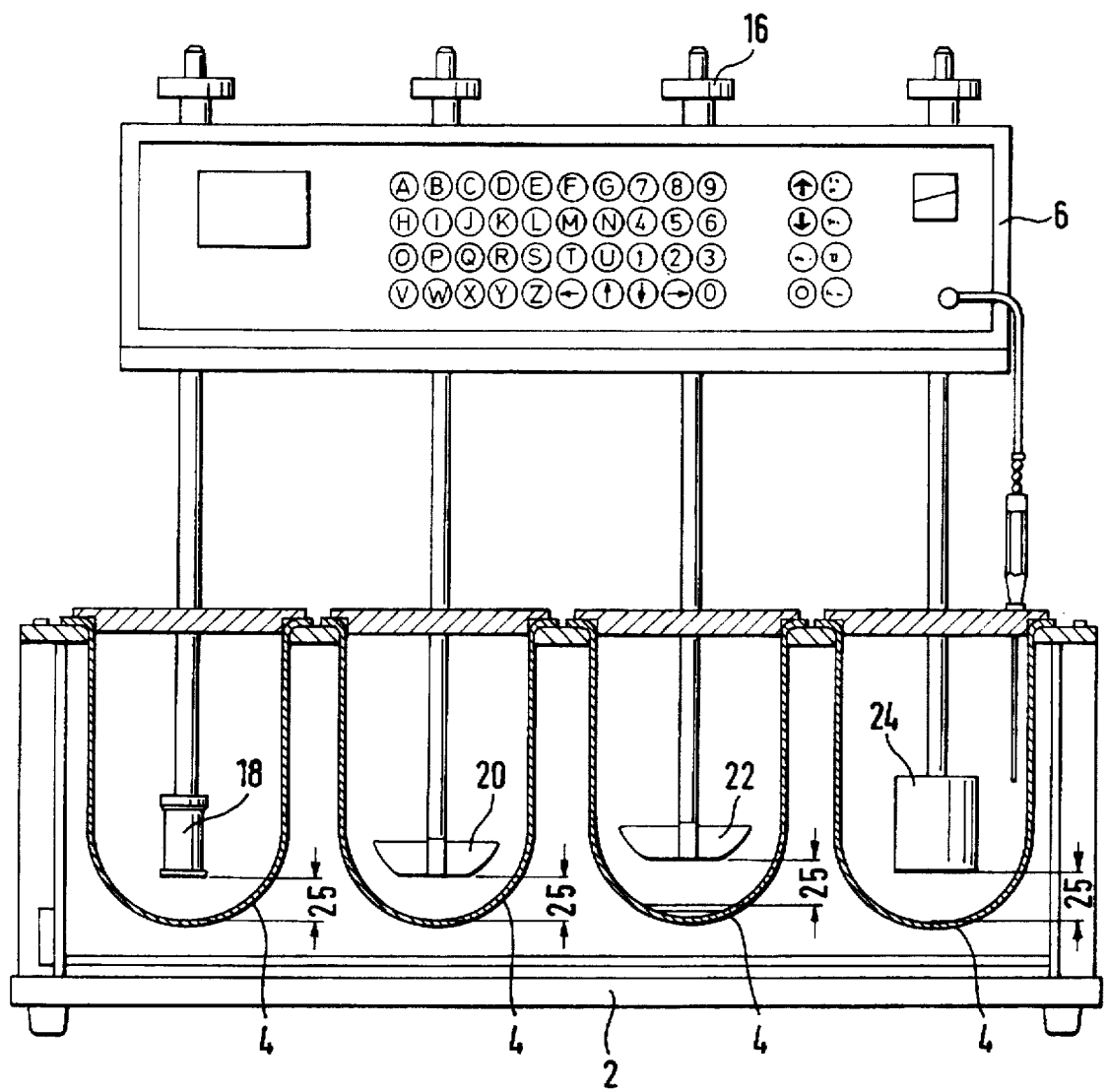
FIG. 2 shows a schematic representation of the dissolution tester after adjustment, the stirring elements being located in a working position.

FIG. 3 further shows in addition to the representation of FIGS. 1 and 2, the arrangement of discharging tubes 26 on frame 28 which is disposed on housing 6 so as to be vertically adjustable via telescopic columns 30,32. Telescopic columns 30, 32 are coupled via toothed belt 34 with stepping motor 36 which moves frame 28 and thus moves discharging tubes 26 to the particular working position in program-controlled manner, in accordance with input data of the filling level and the stirring tool used. The corresponding data of the stirring tool used are entered in the computer in housing 6 during adjustment of the stirring tools, while the data of the filling level of the particular dissolution sample are entered during adjustment of the device for a certain test. The relevant data are therefore available in the computer after being processed by the program and can be transmitted to the stepping motor in the form of stepping pulses.

Figure 4:
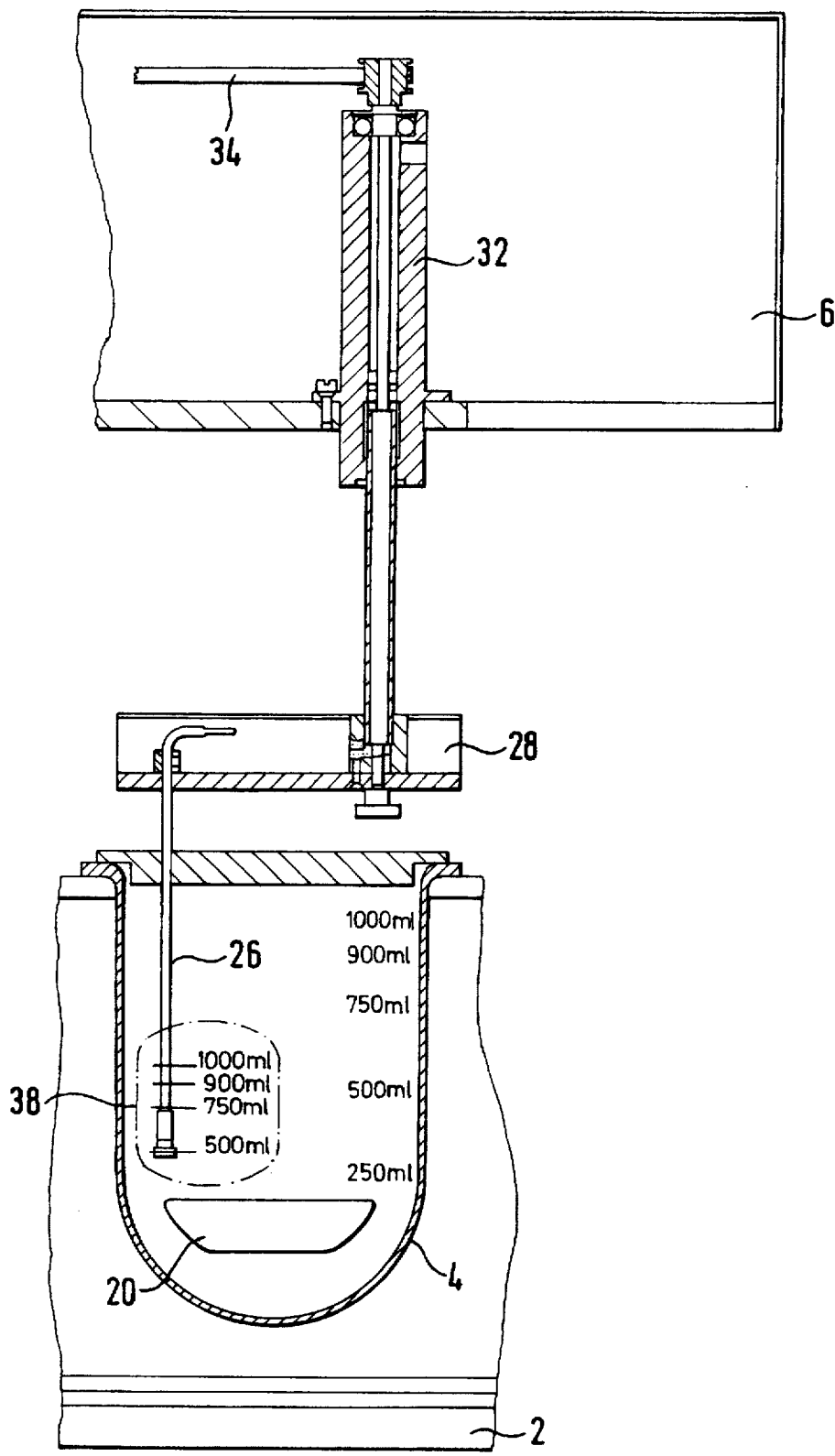
FIG. 4 shows part of the discharging device in detail.

FIG. 4 shows, in greater detail, the relation between the filling levels 1,000 ml, 900 ml, 750 ml and 500 ml and the corresponding working positions of discharging tubes 26 which are likewise designated 1,000 ml, 900 ml, 750 ml and 500 ml at 38 in FIG. 4. It is to be noted that the working positions of discharging tubes 26 are different depending on the stirring tool used. Therefore, the positions shown in FIG. 4 are only correct for a test method in which a paddle is used.

If a basket is used in a test method instead of a paddle, other working positions will result for the discharging tubes.

This makes it apparent that problems arise if these working positions are not moved to in program-controlled manner, as in the present embodiment. One would then either have to use for each test method specially calibrated test vessels in which the working positions of the discharging tubes are marked, or would have to provide several markings for the different stirring tools on one vessel. Both possibilities are insufficiently reliable because they are too unclear.

I claim:

1. A dissolution tester having a plurality of test vessels for receiving dissolution samples, comprising:
   - a plurality of stirring elements for stirring the dissolution samples, the stirring elements being disposed in a vertically adjustable housing,
   - a discharging device with discharging tubes for discharging predetermined volume fractions of the dissolution samples from the test vessels, said discharging tubes being disposed at a predetermined working position in the test vessels in accordance with a filling level of the dissolution sample and the stirring element used,
   - a frame on which the discharging tubes are disposed, the frame being disposed on the housing in vertically adjustable fashion,
   - a motor for moving the frame and the discharging tubes to a working position in program-controlled manner in accordance with input data of the filling level and the stirring element, and
   - a computing device for storing measurement data and predetermined parameters.

2. The dissolution tester of claim 1, wherein the motor is a stepping motor.

3. The dissolution tester of claim 1, wherein the motor is coupled via a toothed belt with two telescopic columns which carry the frame.

* * * * *